United States Patent [19]

Mans

[11] Patent Number: 4,539,999
[45] Date of Patent: Sep. 10, 1985

[54] METHOD AND DEVICE FOR SUBTRACTING A PACER SIGNAL FROM AN ECG SIGNAL

[75] Inventor: Thomas A. Mans, Harrington Park, N.J.

[73] Assignee: Datascope Corp., Paramus, N.J.

[21] Appl. No.: 516,265

[22] Filed: Jul. 22, 1983

[51] Int. Cl.³ ............................................. A61B 5/04
[52] U.S. Cl. ................................. 128/696; 128/902
[58] Field of Search ................ 128/419 PT, 695, 696, 128/697, 902

[56] References Cited
U.S. PATENT DOCUMENTS 3,897,774 8/1975 Burdick et al. .................... 128/697
4,041,328 8/1977 Mads .................................. 128/697

OTHER PUBLICATIONS

Plumb et al., "I.E.E.E. Transactions on Biomedical Engineering", vol. 11, No. 4, Oct. 1964, pp. 157-159.

Primary Examiner—William E. Kamm
Attorney, Agent, or Firm—Fitzpatrick, Cella, Harper & Scinto

[57] ABSTRACT

Disclosed herein is a pacer signal reject circuit wherein an entire ECG waveform signal is applied to one input of an operational amplifier, while only the initial portion of the pacer signal including the main pulse and a portion of the tail, is applied to the second input of such operational amplifier, to cause cancellation of that initial portion from the ECG signal. Also, a synthesized version of the remainder of such pacer tail is generated and applied to the second input. Thus, by isolating the ECG signal from the second input except for a timed period of the pacer signal, and by applying the synthesized tail signal to such second input, the entire pacer signal may be cancelled.

5 Claims, 4 Drawing Figures

METHOD AND DEVICE FOR SUBTRACTING A PACER SIGNAL FROM AN ECG SIGNAL

BACKGROUND OF THE DISCLOSURE

A necessary procedure during medical surgery is to monitor the heart rate of the patient by means of a heart rate meter. A problem exists, however, if the patient has a pacemaker, since the pacer signal may continue to trigger the heart rate meter even if the patient has gone into cardiac arrest. Under these circumstances the heart rate meter would provide an erroneous reading and would falsely indicate the presence of a heartbeat. This problem and its associated risks have been recognized in the past, and attempts to overcome such risks have involved the filtering of the pacer signal from the patient's ECG signal, prior to applying the remainder of the ECG to the heart rate meter. Such filtration is possible when the pacer signal does not have any overshoot, since the pulse width of the pacer signal is extremely narrow as compared to the pulse width of a normal heartbeat. However, some pacemakers provide a pacer signal having an overshoot, also referred to as a "pacer tail", and the bandwidth of such a tail may be of the same order of magnitude as the entire bandwidth of the ECG complex, thus precluding the use of electronic filtering as a means of removing the pacer signal.

Accordingly, an object of the present invention is to inhibit the application of the pacer signal so that the ECG signal applied to the heart rate meter will encompass solely the heartbeat of the patient.

SUMMARY OF THE INVENTION

The present invention provides an improvement over the prior art "pacer reject circuits" by processing an ECG signal to remove the entire pacer signal, including both the pacer pulse itself, as well as the pacer tail. To accomplish this function the rapid rise time or "slew rate" of the main pacer pulse is sensed and utilized to activate a one-shot circuit having an operating time of about 20 milliseconds. The pulse length of this main portion of the pacer signal is on the order of 0.1 to 2 milliseconds so that the duration of the one-shot encompasses the entire period of the main portion of the pacer pulse, together with at least about 18 milliseconds of the tail portion thereof, if such a tail portion exists. The output of the one-shot circuit is utilized to close a switch which feeds the pacer signal of the ECG waveform through a resistor to the positive input terminal of an operational amplifier, while the entire ECG signal is fed on a steady state basis to the negative input terminal of the operational amplifier. An RC circuit is connected between the switch and the operational amplifier so that during the 20 millisecond period that such switch is closed, the capacitor will be charged by the voltage of any tail portion of the pacer signal. The circuit is so designed that the capacitor in the RC circuit will be charged to the same value as the voltage of the tail portion of the pacer signal at the time the one-shot circuit opens the switch. Furthermore, the circuit is so designed that the decay period of the RC circuit will approximate the decay period of the pacer tail, so that both inputs to the operational amplifier will include signals corresponding to the entire wave form of the pacer signal. In this regard, the negative input of the operational amplifier will receive the actual ECG signal, whereas the positive terminal thereof will receive the actual initial pacer pulse, but only a pseudo pacer tail portion, after 20 milliseconds, generated by the RC circuit. These two inputs will be cancelled by the operational amplifier.

It will be appreciated by those skilled in the art, however, that the actual heartbeat of the patient will occur at some time after the 20 millisecond closure of the switch, and therefore, the actual heartbeat will appear at the output of the operational amplifier, even though such heartbeat may occur during the tail portion of the pacer signal period. That is, the actual heartbeat signal will be applied only to the negative input of the operational amplifier, and will therefore appear at the output thereof, because there is no corresponding cancelling heartbeat signal at the positive input. Such output of the operational amplifier may then be applied to the heart rate meter, thereby yielding an accurate indication of the patient's heartbeat during surgery.

BRIEF DESCRIPTION OF THE DRAWINGS

A preferred embodiment of the invention will be described below in conjunction with the accompanying drawings wherein.

DETAILED DESCRIPTION OF THE PREFERRED EMBODIMENT

Figure 1A:
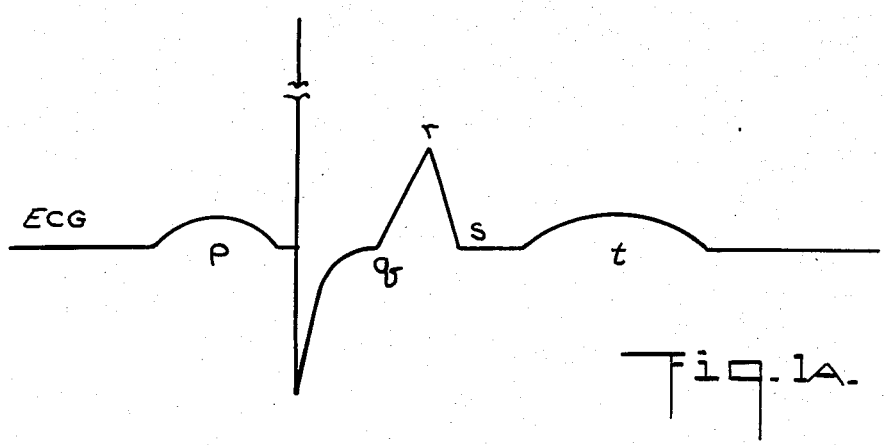
FIG. 1A of the drawings depicts an ECG waveform corresponding to the heartbeat of a patient having a pacemaker.

Various portions of a heartbeat waveform, viewable by means of an ECG, are illustrated in FIG. 1A of the drawings, and are identified by the conventional reference symbols p, q, r, s, and t, which are utilized in the industry. In addition, however, FIG. 1A depicts a typical pacemaker pulse wherein such pulse has an overshoot or "pacer tail", such pacer signal being located, in time, between the p and q portions of the heartbeat waveform. Typically the q, r, s portion of the heartbeat waveform would have a duration from q to s on the order from 70 to 120 milliseconds, and the magnitude of such pulse would be on the order of 0.1 volt to 2.5 volts. The pacer signal carried on the ECG waveform, on the other hand, will have an amplitude for its positive main pulse or 1 volt or greater, while the overshoot may have a maximum magnitude of about 1 volt, and may have a decaying time constant of from 20 to 100 milliseconds. Further in this regard it is noted that certain pacemakers provide reversed polarity signals as compared to the signal indicated in FIG. 1A, but the invention will perform its desired function regardless of such polarity.

Figure 1B:
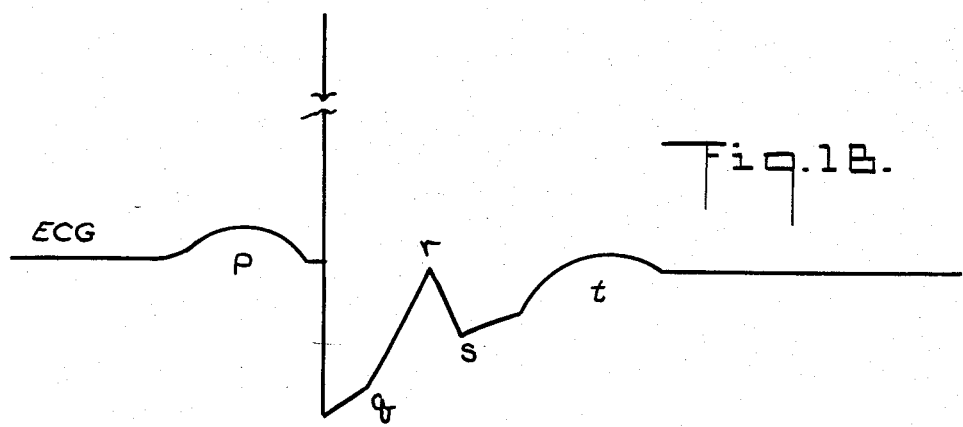
FIG. 1B depicts a possible alternative wave form comparable to that shown in FIG. 1A.

As shown in FIG. 1B of the drawings, it would be possible in view of the various parameters of the pacer signal and of a normal heartbeat signal, for the portion q, r, s of the heartbeat signal to be superimposed on the decaying portion of the pacer tail. With this in mind, it will be appreciated that if the entire portion of the ECG signal which includes the pacer signal is somehow filtered out of the ECG signal, the heartbeat signal may also disappear since it may occur on the decaying portion of the pacer tail.

Figure 2:
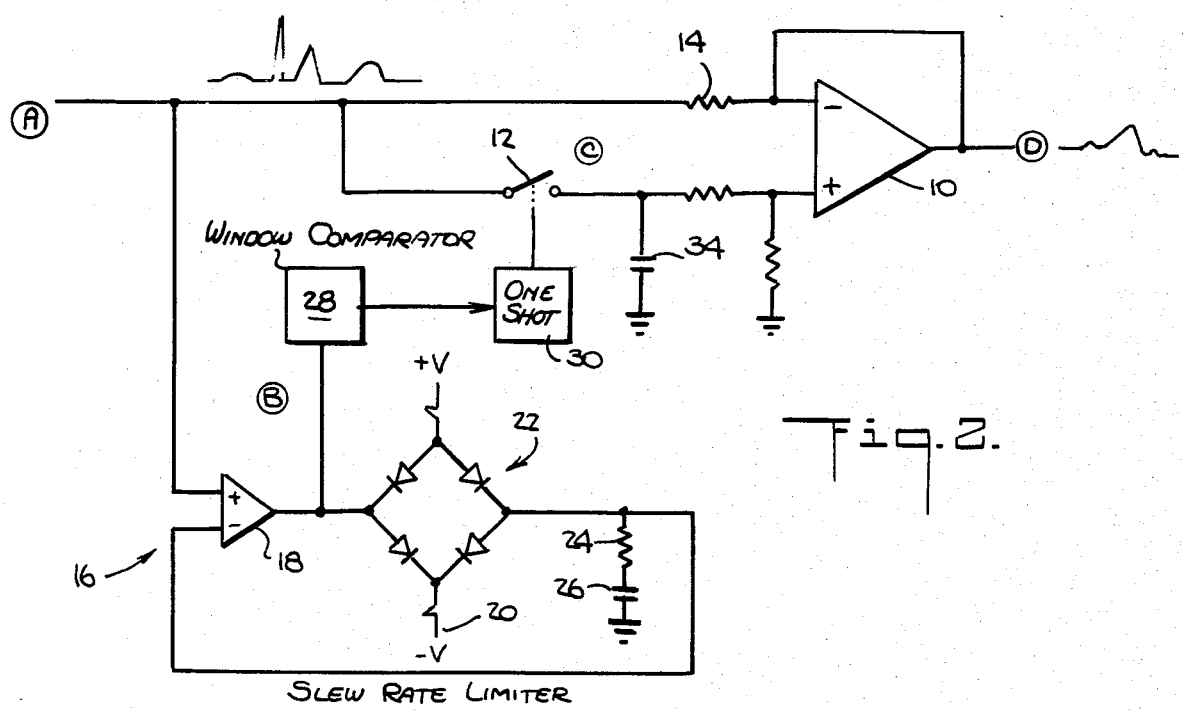
FIG. 2 is a schematic depiction of a preferred embodiment of the invention.
Figure 3:
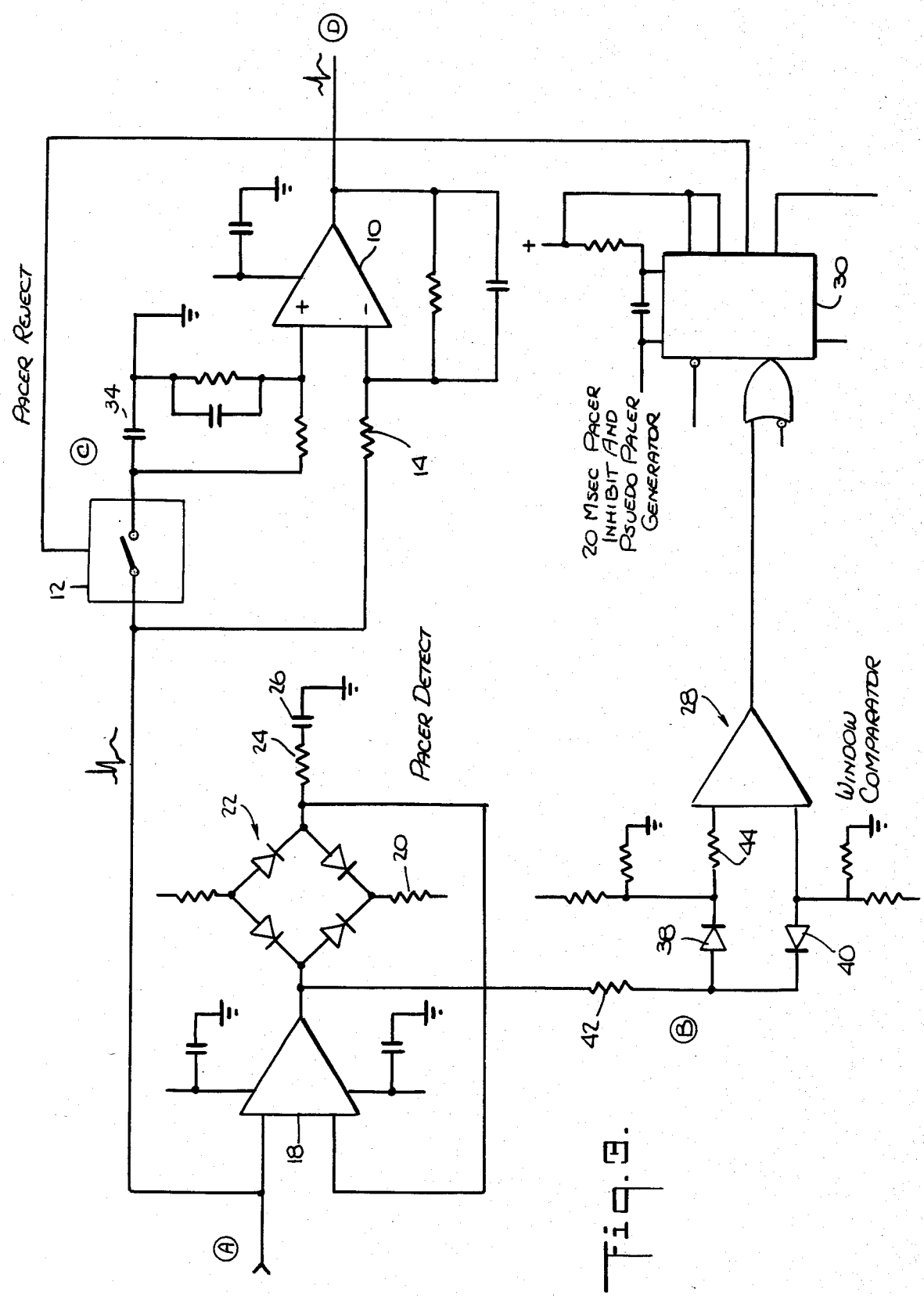
FIG. 3 is a more detailed schematic, similar to FIG. 2, wherein the circuit components and interconnectons are shown with greater specificity.

The present invention, as depicted in FIGS. 2 and 3 of the drawings, effectively subtracts the pacer signal from the ECG complex, but such invention permits the heartbeat portion of the signal to be passed through the circuitry for monitoring purposes.

In the preferred embodiment of the invention, as illustrated in general form in FIG. 2 of the drawings, the ECG complex signal (as shown at A), which includes the patient's heartbeat signal together with a pacer signal, is applied to the "pacer reject circuit". In effect, the circuit operates so that the ECG signal, including the entire pacer signal, is applied to the negative input of the operational amplifier 10, while, during a timed closure of a switch 12, only the initial portion of such pacer signal is applied to the positive input of that operational amplifier. Also, a synthesized tail portion of the pacer signal is applied as a signal to the positive input to the operational amplifier, after the input switch 12 is opened, so that the portions of the heartbeat waveform q, r, s and t are applied only to the negative input of the operational amplifier 10. Therefore, these latter portions of the heartbeat signal, as well as the initial portion p thereof, are carried through to the output D of the circuit, while the actual and the synthesized pacer signals effectively cancel each other.

Such operation of the pacer reject circuit results from the interconnection of components as illustrated in FIG. 2 of the drawings, wherein the entire ECG signal is applied at all times through the resistor 14 to the negative input of the operational amplifier 10. The entire ECG signal is also applied to a slew rate limiter circuit 16, and particularly to the positive input of an operational amplifier 18 therein. The slew rate limiter circuit 16 operates as a voltage follower, so long as the change rate of the input signal does not exceed a predetermined rate. Thus, for example, when the portion p of a heartbeat signal, as depicted in FIG. 1A of the drawings, is applied to the slew rate limiter, the change at the output B of the operational amplifier 18 will follow the input since the change rate is relatively gradual. This function of the circuit results from the fact that the slight increase in voltage at the ouput of the operational amplifier 18 at the time of application of the wave form p thereto will cause an increase in voltage across the resistor 20 of a bridge 22, wherefore a balancing current i will flow through the resistor/capacitor circuit 24, 26, thereby causing a voltage to be applied to the negative input of the operational amplifier 18 so as to cause the output at B to follow the input at A.

On the other hand, when that p-portion of the ECG signal reaches the negative input to the operational amplifier 10 (i.e., prior to the generation of the pacer signal) that signal portion is coupled through the operational amplifier 10 to the output D thereof, as shown in FIG. 2. This results due to the open state of the switch 12, wherein there is no comparable input corresponding to that p-portion of the wave at the positive input to the operational amplifier 10.

If, however, the voltage pulse applied to the operational amplifier 18 exceeds a particular slew rate value, wherein the time constant of the RC circuit 24, 26 cannot follow such a slew rate, then the operational amplifier will become saturated. In such case a large voltage, i.e., the supply voltage, will be seen at the output of the operational amplifier 18 and that voltage increase will be applied to a window comparator 28. In particular, the slew rate for causing saturation may preferably be set at about 1,500 volts/second which is some five times the maximum slew rate of the q, r, s pulse of a normal heartbeat. If the voltage applied to the window comparator exceeds a predetermined level, positive or negative depending on the polarity of the pacer signal, then the comparator 28 will apply a trigger signal to a one-shot circuit 30. The one-shot circuit, having an operational period of about 20 milliseconds is coupled to close the switch 12, whereby such switch 12 is closed for the 20 millisecond period. In this regard, it will be seen that the overall effect of the slew rate limiter, the window comparator, and the one-shot device, is to close the switch 12 as soon as the main pacer pulse is detected in the ECG waveform. As a result, the short-lived initial positive pulse of the pacer signal is coupled through the resistor 14, and through the switch 12 and a resistor 32 to the respective negative and positive inputs of the operational amplifier 10. Since the same signal is applied to both the positive and negative inputs to the operational amplifier 10, the output thereof will be zero.

Since the pulse width of the entire positive portion of the pacer signal is only on the order of about 2 milliseconds, and since the switch 12 is closed for 20 milliseconds, a sizable portion of the pacer tail is coupled through the switch 12 to the operational amplifier 10. In this regard, the capacitor 34 is charged by the pacer tail, so that at the time of termination of the 20 millisecond period of the one-shot 30, when the switch 12 opens, the voltages applied to the positive and negative inputs of the operational amplifier 10 are substantially identical. Furthermore, the RC circuit connected to the positive input of the operational amplifier 10 has a time constant which is the same as the decay period of the pacer tail so that the discharge of the capacitor C is approximately identical to the decay curve of the pacer tail. Consequently, the output of the operational amplifier 10 shows no effect of the pacer signal input thereto.

In contrast, however, the q, r, s, t portions of the ECG signal, which occur more than 20 milliseconds after the initiation of the pacer signal, are applied only to the negative input of the operational amplifier 10, and are isolated from the positive input thereof by the open switch 12. Accordingly, the heartbeat portions p, q, r, s, t which constitute the actual heartbeat signal of the patient, are coupled through to the output D of the operational amplifier 10 for use in activating the heartbeat meter (not shown).

The actual components utilized in the preferred embodiment of the invention are depicted schematically in FIG. 3 of the drawings, wherein it is seen that one-half of a TL082 operational amplifier is utilized as the operational amplifier 18 of the slew rate limiter, while the other half of that operational amplifier is utilized in the window comparator 28. Furthermore, in the preferred embodiment of the invention the bridge diodes of the slew rate limiter are connected through resistors of 115K ohms to positive and negative 7.5 volt sources, while the resistor 24 has a value of about 1K ohm and the capacitor 26 has a value of about 0.1 microfarads. The slew rate limiter circuit output is coupled from the output of the operational amplifier 18 to a pair of input diodes 38 and 40 through a 1K resistor 42. The input resistor 44 to the operational amplifier of the window comparator has a value of 47k, as do each of the bias resistors connected to the inputs to the operational amplifier of the window comparator.

The 20 millisecond one-shot device constitutes an integrated circuit, type number 4538, connected as shown in FIG. 3 of the drawings, and having a resistor and a capacitor of values 200K ohms and 0.1 microfarads connected to its positive supply source, at terminals 1 and 2 thereof. The output of the one-shot is taken from terminal 6 thereof and applied to the control terminal 6 of a switch device constituting a 4066 integrated circuit, connected as shown in FIG. 3. The two input resistors for the operational amplifier 10 have values of 200K ohms, while the capacitor 34 has a value of 0.033 microfarads. Furthermore, an RC circuit comprising a resistor having a value of 392K and a capacitor having a value of 0.01 microfarads is connected in parallel between the positive input to the operational amplifier 10 and ground. The feedback circuit for the operational amplifier 10 constitutes a parallel circuit comprising a resistor having a value of 392K and a capacitor having a value of 0.01 microfarads.

While a preferred embodiment of the invention has been described herein, in conjunction with the accompanying drawing figures, it will be appreciated by those skilled in the art that other modifications of such circuitry can be assembled to perform the required functions of the invention, but that such modifications fall within the scope of Applicant's invention.

I claim:

1. A pacer signal reject device for subtracting a pacer signal from an ECG signal, comprising:

subtraction circuit means having first and second inputs and an output wherein a signal applied to said second input is subtracted from a signal applied to said first input, and wherein a remainder signal is provided at said output;

first signal applying means for applying a patient's ECG signal, including actual heartbeat pulses and pacer signals, to said first input of said subtraction circuit means; and second signal applying means for applying a signal corresponding to said pacer signal to said second input of said subtraction circuit means, wherein the pacer signal is subtracted from said ECG signal, by said subtraction circuit means, and wherein said output of said subtraction circuit means provides an output corresponding only to the patients actual heartbeat pulses;

said second signal applying means comprises switch means coupled between said first and second inputs of said subtraction circuit means, means for detecting the initial rise-time of the pacer signal and for generating a detection signal corresponding thereto, and means for applying said detection signal to close said switch means for a timed period, wherein said timed period is in excess of the period of the main pulse of said pacer signal.

2. A pacer signal reject device, as set forth in claim 1, wherein said detecting means comprises a slew rate circuit means having an input coupled to receive said ECG signal, and having an output for generating said detection signal when said main pulse of said pacer signal is detected.

3. A pacer signal reject device for subtracting a pacer signal from an ECG signal, comprising:

subtraction circuit means having first and second inputs and an output wherein a signal applied to said second input is subtracted from a signal applied to said first input, and wherein a remainder signal is provided at said output;

first signal applying means for applying a patient's ECG signal, including actual heartbeat pulses and pacer signals, to said first input of said subtraction circuit means; and second signal applying means for applying a signal corresponding to said pacer signal to said second input of said subtraction circuit means, wherein the pacer signal is subtracted from said ECG signal, by said subtraction circuit means;

and further comprising RC circuit means connected between said switch means and said second input of said subtraction circuit for storing a voltage corresponding to the voltage of the pacer signal at the end of said timed period, wherein said stored voltage will correspond to the voltage of any pacer tail of the pacer signal at the end of said timed period, and wherein said RC circuit provides a decay time-constant for said voltage which corresponds to the decay time constant of the pacer tail, said RC circuit thereby providing a pseudo pacer tail signal, after said switch means is opened, corresponding to the remainder of any pacer tail conducted through said switch during said timed period that said switch means is closed, wherein said output of said subtraction circuit means provides an output corresponding only to the patient's actual heartbeat pulses.

4. A pacer signal reject device as set forth in claim 3 wherein said detecting means comprises a slew rate circuit means having an input coupled to receive said ECG signal, and having an output for generating said detection signal when said main pulse of said pacer signal is detected.

5. A pacer signal reject device, as set forth in claim 4, wherein said slew rate circuit means is set to generate said detection signal when a slew rate exceeding a rate of the order of 1,500 volts/second is detected.

* * * * *